United States Patent [19] | [11] Patent Number: 4,482,717
Dinkel et al. | [45] Date of Patent: * Nov. 13, 1984

[54] METHOD FOR THE PRODUCTION OF 3-PICOLINE

[75] Inventors: Rolf Dinkel, Münchenstein; Hilmar Roedel, Therwil; James I. Grayson, Visp, all of Switzerland

[73] Assignee: Lonza Ltd., Gampel, Switzerland

[*] Notice: The portion of the term of this patent subsequent to Nov. 6, 2001 has been disclaimed.

[21] Appl. No.: 493,505

[22] Filed: May 11, 1983

Related U.S. Application Data

[63] Continuation-in-part of Ser. No. 337,769, Jan. 7, 1982, abandoned.

[30] Foreign Application Priority Data

Jan. 9, 1981 [CH] Switzerland ............................ 104/81
Mar. 12, 1981 [CH] Switzerland ........................ 1685/81

[51] Int. Cl.³ .................. C07D 213/08; C07D 213/10
[52] U.S. Cl. .................................................. 546/251
[58] Field of Search ......................................... 546/251

[56] References Cited

U.S. PATENT DOCUMENTS 4,337,342 6/1982 Dinkel ................................. 546/251
4,370,481 1/1983 Dinkel ................................ 546/251

Primary Examiner—Robert T. Bond
Attorney, Agent, or Firm—Fisher, Christen & Sabol

[57] ABSTRACT

Method for the production of 3-picoline wherein a first educt, consisting of at least one acetaldehydeacetal with or without acetaldehyde and/or crotonaldehyde, is reacted with a second educt, consisting of at least one formaldehydeacetal and/or hexamethylenetetramine with or without formaldehyde, in a liquid, aqueous phase at a temperature of 180° to 280° C. in a closed vessel. The reaction is conducted in the presence of ammonia and/or ammonium ions. The reaction is also conducted in the presence of an anion or anions of an inorganic and/or organic acid or acids, which at 20° C. have an acid dissociation constant of $10^6$ to $10^{-12}$.

19 Claims, No Drawings

METHOD FOR THE PRODUCTION OF 3-PICOLINE

This is a continuation-in-part of U.S. application Ser. No. 337,769, filed on Jan. 7, 1982 now abandoned.

BACKGROUND OF THIS INVENTION

1. Field of this Invention

This invention relates to a process for the production of 3-picoline.

2. Prior Art

Pyridine bases represent important intermediate products in the chemical industry, for example, in the case of the production of nicotinic acid or nicotinic acid amide. Various processes are known for the production of pyridine bases.

Nowadays, 2-methyl-5-ethylpyridine is produced on a large scale in the liquid phase process from acetaldehyde or paraldehyde and ammonia in the presence of very diverse types of catalysts, such as, ammonium salts. Small quantities of 2- and 4-picoline are obtained as by-products.

2- and 4-picoline are produced in gas phase reactions at a temperature of about 400° C. from acetaldehyde and ammonia with the use of solid bed or moving bed catalysts on the basis of aluminum silicate.

For the production of pyridine as well as of 3-picoline, which achieves ever greater importance, gas phase reactions are currently used whereby through the addition of formaldehyde to the acetaldehyde, the formation of 2- and 4-picoline is suppressed in favor of 3-picoline. These reactions also take place in a solid bed or moving bed with aluminum silicate as a catalyst at a temperature of about 400° C. According to these processes, yields of 3-picoline in the order of magnitude of at most 40 to 44 percent is achieved. Beside that, large quantities of pyridine are obtained.

It is further known that one may start out, instead of from saturated aldehydes, from unsaturated aldehydes, such as, acrolein or croton-aldehyde. These reactions take place in the gaseous phase at high temperatures; the yields are essentially as high as in the case of the use of saturated aldehydes as starting material.

BROAD DESCRIPTION OF THIS INVENTION

The main object of this invention is to produce 3-picoline in high yields, whereby the formation of pyridine is suppressed as much as possible. Other objects and advantages of this invention are set out herein or are obvious herefrom to one ordinarily skilled in the art.

The objects and advantages of this invention are achieved by the process of this invention.

This invention involves a process for the production of 3-picoline wherein a first educt, consisting of at least one acetaldehydeacetal with or without acetaldehyde and/or crotonaldehyde, is reacted with a second educt, consisting of at least one formaldehydeacetal and/or hexamethylenetetramine with or without formaldehyde, in a liquid, aqueous phase at a temperature of 180° to 280° C. in a closed vessel. The reaction is conducted in the presence of ammonia and/or ammonium ions. The reaction is also conducted in the presence of an anion or anions of an inorganic and/or organic acid or acids, which at 20° C. have an acid dissociation constant of $10^6$ to $10^{-12}$.

In this invention, acetaldehyde includes its polymers, such as, paraldehyde. In this invention, formaldehyde includes its polymers, such as, trioxane.

Preferably the required individual component of each of the first and second educts is always only used individually; thus, in the case of the first educt, preferably an acetaldehydeacetal is used by itself, and in the case of the second educt, preferably a formaldehydeacetal or hexamethylenetetramine is used by itself.

In order to insert into the reaction solution the anions (important for the reaction) of inorganic and/or organic acids, which at 20° C. have an acid dissociation constant of $10^6$ to $10^{-12}$, the corresponding water-soluble alkali and/or ammonium salts of these acids are added to the reaction solution.

Salts of acids useful in this invention are, for example: the sodium, potassium or ammonium salts of the pentaboric acid, such as ammonium pentaborate; carboxylic acid, such as ammonium carbonate; phosphoric acid, such as, potassium dihydrogen phosphate, ammonium dihydrogen phosphate, dipotassium hydrogen phosphate and diammonium hydrogen phosphate; sulfuric acid, such as sodium hydrogen sulfate and ammonium sulfate; fluoric acid, such as sodium flouride, ammonium flouride and ammonium hydrogen difluoride; hydrochloric acid, such as ammonium chloride; hydrobromic acid, such as ammonium bromide; heptamolybdic acid, such as ammonium heptamolybdate; formic acid, such as ammonium formiate; acetic acid, such a sodium acetate and ammonium acetate; propionic acid, such as ammonium propionate; butyric acid, such as ammonium butyrate; succinic acid, such as disodium succinate and diammonium succinate; adipic acid, such as diammonium adipinate; benzoic acid, such as sodium benzoate and ammonium benzoate; phthalic acid, such as diammonium phthalate; terephthalic acid, such as diammonium terephthalate; nicotinic acid, such as ammonium nicotinate; and isonicotinic acid, such as ammonium isonicotinate.

For the formation of 3-picoline from an acetaldehydeacetal with or without acetaldehyde and/or crotonaldehyde with a formaldehydeacetal and/or hexamethylenetetramine with or without formaldehyde, the presence of ammonia and/or ammonium ions is necessary. For ammonia, which may be used either in a gaseous form or as an aqueous solution, it is sufficient whenever alkali salts of the mentioned acids are used. However, it is also possible to use mixtures of alkali salts and ammonium salts. Whenever ammonia is not used, ammonium salts or mixtures of ammonium salts and alkali salts are to be used. Whenever liquid starting materials which are not mutually mixable are used, it is advantageous for homogenization to use small quantities of homogenization agents, such as, alcohols, cyclic ethers and preferably preformed 3-picoline, or to feed in the non-miscible liquid starting materials into the reactor using separate pumps.

According to the process of this invention, 3-picoline is surprisingly obtained in yields up to about 65 percent and the formation of pyridine is almost completely suppressed (below 1 percent). As a by-product, 3-ethylpyridine as well as small quantities of 2,5-dimethylpyridine, 3,5-dimethylpyridine and 2-methyl-5-ethyl pyridine are obtained.

The process of this invention is carried out effectively with a molar ratio of acetaldehyde acetal (with or without acetaldehyde) to formaldehyde acetal (with or without formaldehyde) of from 1:0.5 to 1:1.2, preferably from 1:0.8 to 1:1. Whenever crotonaldehyde is used in place of acetaldehyde acetal (with and/or without acetaldehyde), the molar ratio of crotonaldehyde to formaldehyde acetal (with or without formaldehyde) is from 1:1 to 1:2.4. Whenever hexamethylenetetramine is used instead of formaldehyde acetal, then the molar ratio of acetaldehyde acetal (with or without acetaldehyde) to hexamethylenetetramine (with or without formaldehyde) is from 1:0.083 to 1:0.2.

The reaction temperature advantageously lies between 180° and 280° C., more effectively between 205° and 240° C., and preferably between 225° and 235° C. The reaction is carried out in the liquid phase (aqueous phase) under a pressure which occurs during the reaction in the closed vessel at a predetermined temperature. It is advantageous to stir the reaction mixture during the reaction.

The quantity of ammonia and/or ammonium ions is from 0.5 to 3 moles of ammonia and/or ammonium ions per mole of educt, and preferably is from 0.5 to 2.0 moles per mole of educt.

The quantity of the anions of the inorganic and/or organic acids effectively lies between 0.1 and 3 moles, preferably between 0.2 and 1.0 mole per mole of educt.

The starting pH value of the aqueous reaction solution preferably is between 5.0 and 12.5.

The addition of the acetal is preferably accomplished according to a measurement of its consumption. Thus, for example, it is favorable in the case of the use of a 2-liter container and 350 ml of acetal, to add this acetal continuously during a period of 30 to 90 minutes. In the case of other conditions, corresponding addition-times can be selected.

At the end of the desired reaction period, the temperature is lowered to approximately ambient temperature and the 3-picoline is obtained in a known or suitable manner from the reaction mixture. One method involves first bringing the pH value of the water phase into the basic area (i.e., a basic pH) and then extracting the organic material from the aqueous reaction mixture with an organic solvent, for example, benzol, toluene, xylene, methylene chloride, chloroform, ether and similar solvents. The organic solvent is then evaporated and 3-picoline is obtained by fractional distillation. Within the scope of this invention, any other separation methods for obtaining the product can be used.

One advantage of the process of this invention is the fact that the aqueous phase obtained after the extraction of the reaction mixture with an organic solvent can be returned into the reactor after re-enrichment with ammonia and/or ammonium ions. The aqueous salt phase is composed of the original quantity of water present in the salt solution, the unreacted quantity of ammonia and/or ammonium salt, the optionally-present metal salt, and the liberated acid of the ammonium salt participating in the reaction as well as one mole of water for each mole of the educts consumed during the reaction. The aqueous salt phase therefore can be concentrated with the help of any known or suitable process, for example, by evaporation in order to remove the water formed as a consequence of the condensation reaction.

Re-enrichment of ammonia and/or ammonium salt can then be achieved through the fact that gaseous ammonia can be inserted in the aqueous solution at ambient temperature with reformation of the ammonium salt from the optionally present acid.

Although this invention has been described as a noncontinuous process, this process can also be operated continuously within the scope of this invention. In the case of carrying out the process on a continuous basis, the reaction participants are introduced continuously into a suitable pressure reactor, from which the reaction mixture is continuously withdrawn. The reaction products are separated from that, the aqueous salt phase is concentrated, and the unchanged reaction participants are then supplemented and returned to the reaction vessel. The continuous process can be carried out in any reactor which permits a thorough intermixing of the reaction participants with vigorous stirring, for example, in a continuously stirred tank reactor.

This invention also involves a composition useful in the process of this invention. The composition includes: (i) a member of the group consisting of (a) at least one acetaldehydeacetal, (b) at least one acetaldehyde acetal and crotonaldehyde and (c) at least one acetaldehydeacetal and acetaldehyde; (ii) a member of the group consisting of (d) at least one formaldehydeacetal, (e) hexamethylenetetramine, (f) at least one formaldehydeacetal and formaldehyde and (g) hexamethylenetetramine and formaldehyde; (iii) water; (iv) ammonia and/or ammonium ions; and (v) at least one anion of an inorganic and/or organic acid or acids, which at 20° C. show an acid dissociation constant of $10^6$ to $10^{-12}$. Preferably a homogenization agent is present in the composition. Also preferably the composition has a pH of 5 to 12.5.

By way of summary, this invention involves a process for the production of 3-picoline from acetaldehydeacetal with or without acetaldehyde and/or crotonaldehyde on the one hand and a formaldehydeacetal and/or hexamethylenetetramine with or without formaldehyde on the other hand in the liquid phase.

DETAILED DESCRIPTION OF THIS INVENTION

As used herein, all parts, percentages, ratios and proportions are on a weight basis unless otherwise stated herein or otherwise obvious herefrom to one ordinarily skilled in the art.

EXAMPLE 1

1140 ml of a 3.40 molar aqueous solution of diammonium hydrogen phosphate (pH 8.35) was heated in a 2-liter autoclave to 230° C. and stirred at 1500 rpm. Into this solution, a mixture of 117.7 g of acetaldehyde, 49.8 g of hexamethylene tetramine and 200 g of water was continuously pumped within a period of 55 minutes (calculated molar ratio acetaldehyde: formaldehyde=1:0.78). At the same time, the reaction pressure varied between 33 and 39 bar. After complete addition of the educt mixture, the reaction mass continued to be stirred for 10 minutes at 230° C. and was then cooled to ambient temperature. Finally, extraction was made with 3×100 ml of methylene chloride and a gas chromatographic analysis of the united methylene chloride extracts was made. The following products resulted with a yield related either to the amount of acetaldehyde (A) used or to the amount of hexamethylenetetramine (F) used, depending on the aldehyde need: pyridine, 1.0 percent (A); 3-picoline, 59.4 percent (F); 3-ethyl pyridine, 22.8 percent (A); 2,5-lutidine, 4.0 percent (A); 3,5-lutidine, 0.7 percent (F); and 2-methyl-5-ethylpyridine, 1.8 percent (A). The aqueous phase has a pH of 9.2 after the extraction. All of the gas chromatographic analyses were carried out with the use of an internal standard as well as with due consideration of surface correction factors.

EXAMPLE 2

1140 ml of a 3.40 molar aqueous solution of diammonium hydrogen phosphate (pH 8.35) was heated in a 2-liter autoclave to 230° C. and stirred at 1500 rpm. Into this solution of mixture of 117.7 g of paraldehyde, 49.8 g of hexamethylene tetramine, 130 g of water and 120 g of ethanol were pumped in continuously within a period of 60 minutes (calculated molar ratio acetaldehyde:formaldehyde=1:0.80). At the same time, the reaction pressure varied between 35 and 44 bar. After complete addition of the educt mixture, the reaction mass continued to be stirred for 10 minutes at 230° C. and was then cooled to ambient temperature. Finally, extraction was made with 3×100 ml of methylene chloride and a gas chromatographic analysis of the combined methylene chloride extracts was made. The following products resulted with a yield related to the amount of paraldehyde (A) used or to the amount of hexamethylenetetramine (F) used, depending on the aldehyde need: pyridine, 0.8 percent (A); 3-picoline, 65.6 percent (F); 3-ethyl pyridine, 19.0 percent (A); 2,5-lutidine, 3.4 percent (A); 3,5-lutidine, 0.8 percent (F); and 2-methyl-5-ethyl pyridine, 2.8 percent (A). The aqueous phase had a pH of 9.4 after extraction.

EXAMPLE 3

1140 ml of a 3.40 molar aqueous solution of diammonium hydrogen phosphate (pH 8.35) was heated in a 2-liter autoclave to 220° C. and stirred at 1500 rpm. Into this solution, a mixture of 120.0 g of paraldehyde, 49.8 g of hexamethylenetetramine, 120 g of water and 120 g of ethanol was pumped within a period of 59 minutes (calculated molar ratio acetaldehyde: formaldehyde=1:0.79). At the same time, the reaction pressure varied between 26 and 40 bar. After the complete addition of the educt mixture, the reaction mass continued to be stirred for 10 minutes at 220° C. and was then cooled to ambient temperature. Finally, extraction was made with 3×100 ml of methylene chloride and a gas chromatographic analysis of the combined methylene chloride extracts took place. The following products resulted with a yield related to the amount of paraldehyde (A) used or to the amount of hexamethylenetetramine (F) used, depending on the aldehyde need: pyridine, 0.3 percent (A); 3-picoline, 51.4 percent (F); 3-ethylpyridine, 6.0 percent (A); 2,5-lutidine, 1.4 percent, (A); 3,5-lutidine, 2.7 percent (F); and 2-methyl-5-ethylpyridine, 6.8 percent (A). The aqueous phase had a pH of 9.3 after the extraction.

EXAMPLE 4

1140 ml of a 3.40 molar aqueous solution of diammonium hydrogen phosphate (pH 8.35) was heated in a 2-liter autoclave to 230° C. and was stirred at 1500 rpm. Into this solution, a mixture of 117.7 g of acetaldehyde and 162.2 g of formaldehyde dimethylacetal [also termed dimethylacetal formaldehyde or dimethoxy methane, $CH_2(OCH_3)_2$] was pumped within a period of 47 minutes (molar ratio=1:0.74). At the same time, the reaction pressure varied between 33 and 40 bar. After the complete addition of the educt mixture, the reaction mass continued to be stirred for 10 minutes at 230° C. and was then cooled to ambient temperature. Finally, extraction was made with 2×100 ml of methylene chloride and a gas chromatographic analysis of the combined methylene chloride extracts was accomplished. The following products resulted with a yield related to the amount of acetaldehyde (A) used or to the amount of formaldehyde dimethylacetal (F) used, depending on the aldehyde need: pyridine, 0.9 percent (A); 3-picoline, 51.2 percent (F); 3-ethylpyridine, 24.6 percent (A); 2,5-lutidine, 4.6 percent (A); 3,5-lutidine, 0.8 percent (F); and 2-methyl-5-ethyl pyridine, 3.9 percent (A).

EXAMPLE 5

1140 ml of a 2.40 molar aqueous solution of diammonium hydrogen phosphate (pH 8.35) was heated in a 2-liter autoclave to 230° C. and stirred at 1500 rpm. Into this solution, a mixture of 117.7 g paraldehyde and 162.2 g of formaldehyde diethylacetal was continuously pumped within a period of 64 minutes (calculated molar ratio acetaldehyde: formaldehyde=1:0.74). At the same time the reaction pressure varied between 33 and 40 bar. After complete addition of the educt mixture, the reaction mixture continued to be stirred for 10 minutes at 230° C. and was then cooled to ambient temperature. Finally, an extraction was made with 3×100 ml of methylene chloride and a gas chromatographic analysis of the combined methylene chloride extracts was accomplished. The following products resulted with a yield related to the amount of paraldehyde (A) used or to the amount of formaldehyde diethylacetal (F) used, depending on the aldehyde need: pyridine, 1.0 percent (A); 3-picoline, 53.6 percent (F); 3-ethylpyridine, 23.9 percent (A); 2,5-lutidine, 4.3 percent (A); 3,5-lutidine, 0.6 percent (F); and 2-methyl-5-ethylpyridine, 2.5 percent (A).

EXAMPLE 6

855 ml of a 3.4 molar aqueous solution of diammonium hydrogen phosphate (pH 8.35) was heated in a 2-liter autoclave to 230° C. and stirred at 1500 rpm. Into this solution, a mixture of 160.0 g of acetaldehyde dimethylacetal, 160.0 g of a 30.0 percent aqueous formaldehyde solution and 22.5 g of 3-picoline was continuously pumped within a period of 60 minutes (molar ratio of acetaldehyde dimethylacetal: formaldehyde=1:0.94). At the same time the reaction pressure varied between 33 and 39 bar. After complete addition of the educt mixture, the reaction mass continued to be stirred for 10 minutes at 230° C. and was then cooled to ambient temperature. Finally, an extraction was made with 3×100 ml of methylene chloride and a gas chromatographic analysis of the combined methylene chloride extracts was accomplished. The following products resulted with a yield related to the amount of acetaldehydedimethylacetal (A) used or to the amount of formaldehyde (F) used, depending on the aldehyde need: pyridine, 1.1 percent (A); 3-picoline, 54.9 percent (F) (without the portion for homogenization); 3-ethylpyridine, 12.7 percent (A); 2,5-lutidine, 2.6 percent (A); 3,5-lutidine, 1.2 percent (F); and 2-methyl-5-ethylpyridine, 0.6 percent (A).

EXAMPLE 7

1140 ml of a 3.40 molar aqueous solution of diammonium hydrogen phosphate (pH 8.35) was heated in a 2-liter autoclave to 230° C. and stirred at 1500 rpm. Into this solution, a mixture of 160.0 g of acetaldehyde diethylacetal, 106.6 g of a 30 percent formaldehyde solution, 50.0 g of 3-picoline and 50 g of ethanol was continuously pumped within a period of 59 minutes (molar ratio acetaldehyde diethylacetal: formaldehyde=1:0.80). At the same time, the reaction pressure varied between 33 and 42 bar. After complete addition of the educt mixture, the reaction mass continued to be stirred for 10 minutes at 230° C. and was then cooled to ambient temperature. Finally, extraction was made three times with 100 ml of methylene chloride, and a gas chromatographic analysis of the combined methylene chloride extracts was made. The following products resulted with a yield related to the amount of acetaldehyde diethylacetal (A) used or to the amount of formaldehyde (F) used, depending on the aldehyde need: pyridine, 0.9 percent (A); 3-picoline, 38.3 percent (F) (without the portion for homogenization); 3-ethylpyridine, 24.6 percent (A); 2,5-lutidine, 4.6 percent (A); 3,5-lutidine, 1.4 percent (F); and 2-methyl-5-ethylpyridine, 3.1 percent (A).

EXAMPLE 8

1140 ml of aqueous solution containing 157.4 g of sodium hydrogen sulfate and 85.1 g of ammonia (pH of the solution=10.8) was heated in a 2-liter autoclave to 230° C. and stirred at 1500 rpm. A mixture of 117.7 g of acetaldehyde and 171.0 g of formaldehyde dimethylacetal was continuously pumped into this solution within a period of 65 minutes (calculated molar ratio acetaldehyde: formaldehyde=1:0.80). At the same time the reaction pressure varied between 43 and 45 bar. After complete addition of the educt mixture, the reaction mass continued to be stirred for 10 minutes at 230° C. and was then cooled to ambient temperature. Finally, extraction was accomplished with 3×100 ml of methylene chloride and a gas chromatographic analysis of the combined methylene chloride extracts was made. The following products resulted with a yield related to the amount of acetaldehyde (A) used or to the amount of formaldehyde dimethylacetal (F) used, depending on the aldehyde need: pyridine, 2.1 percent (A); 3-picoline, 53.4 percent (F); 3-ethylpyridine, 17.7 percent (A); 2,5-lutidine, 6.8 percent (A); 3,5-lutidine, 1.0 percent (F); and 2-methyl-5-ethyl-pyridine, 3.5 percent (A).

EXAMPLE 9

1140 ml of aqueous solution containing 155.1 g of potassium dihydrogen phosphate and 85.1 g of ammonia (pH of the solution=10.95) was heated in a 2-liter autoclave to 230° C. and stirred at 1500 rpm. A mixture of 117.7 g of acetaldehyde and 171.0 g of formaldehyde dimethylacetal was continuously pumped into this solution within a period of 65 minutes (calculated molar ratio acetaldehyde: formaldehyde=1:0.80). At the same time the reaction pressure varied between 47 and 52 bar. After complete addition of the educt mixture, the reaction mass continued to be stirred for 10 minutes at 230° C. and was then cooled to ambient temperature. Finally, an extraction was accomplished with 3×100 ml of methylene chloride and a gas chromatographic analysis of the combined methylene chloride extracts was made. The following products resulted with a yield related to the amount of acetaldehyde (A) used or to the amount of formaldehyde dimethylacetal (F) used, depending on the aldehyde need: pyridine, 1.3 percent (A); 3-picoline, 19.3 percent (F); 3-ethylpyridine, 32.9 percent (A); 2,5-lutidine, 9.3 percent (A); 3,5-lutidine, 0.4 percent (F); and 2-methyl-5-ethylpyridine, 20.8 percent (A).

EXAMPLE 10

1140 ml of a 3.40 molar aqueous ammonium acetate solution (pH 7.55) was heated in a 2-liter autoclave to 230° C. and stirred at 1500 rpm. Into this solution, a mixture of 96.0 g of paraldehyde, 39.8 g of hexamethylenetetramine, 104 g of water and 100 g of ethanol was continuously pumped within a period of 51 minutes (calculated molar ratio acetaldehyde: formaldehyde=1:0.80). At the same time, the reaction pressure varied between 25 and 32 bar. After a complete addition of the educt mixture, the reaction mass continued to be stirred for 10 minutes at 230° C. and was then cooled to ambient temperature. Finally, extraction was made three times with 100 ml of methylene chloride and a gas chromatographic analysis of the combined methylene chloride extracts were accomplished. The following products resulted with a yield related to the amount of paraldehyde (A) used or to the amount of hexamethylenetetramine (F) used, depending on the aldehyde need: pyridine, 1.0 percent (A); 3-picoline, 56.3 percent (F); 3-ethylpyridine, 18.5 percent (A); 2,5-lutidine, 5.1 percent (A); 3,5-lutidine, 0.6 percent (F); and 2-methyl-5-ethylpyridine, 2.7 percent (A).

EXAMPLE 11

1140 ml of a 3.40 molar aqueous solution of diammonium hydrogen phosphate (pH 8.35) was heated in a 2-liter autoclave to 220° C. and stirred at 1500 rpm. A mixture of 200.0 g of acetaldehyde diethylacetal and 105.5 g of formaldehyde dimethylacetal was continuously pumped into this solution within a period of 55 minutes (calculated molar ratio acetaldehyde: formaldehyde=1:0.80). At the same time the reaction pressure varied between 37 and 38 bar. After complete addition of the aldehyde mixture, the reaction mass continued to be stirred for 10 minutes at 220° C. and was then cooled to ambient temperature. Finally, an extraction was accomplised with 3×100 ml of methylene chloride as well as a gas chromagraphic analysis of the combined methylene chloride extracts, whereby the following products resulted with a yield related to the amount of acetaldehyde diethylacetal (A) used or to the amount of formaldehyde dimethylacetal (F) used, depending on the aldehyde need: pyridine, 1.0 percent (A); 3-picoline, 35.7 percent (F); 3-ethylpyridine, 34.4 percent (A); 2,5-lutidine, 7.4 percent (A); 3,5-lutidine, 0.3 percent (F); and 2-methyl-5-ethylpyridine, 10.6 percent (A).

EXAMPLE 12

1140 ml of a 3.40 molar solution of diammonium hydrogen phosphate (pH 8.4) was heated in a 2-liter autoclave to 230° C. and stirred at 1500 rpm. 237.0 g of acetaldehyde diethylacetal was continuously fed into this solution with a first pump and mixture of 38.8 g of hexamethylenetetramine and 103 g of water was continuously fed using a second pump within a period of 60 minutes (calculated molar ratio acetaldehyde: formaldehyde=1:0.85). At the same time, the reaction pressure varied between 32 and 42 bar. After complete addition of the educts, the reaction mass continued to be stirred for 10 minutes at 230° C. and was then cooled to ambient temperature. Finally, extraction took place with 3×100 ml of methylene chloride and a gas chromatographic analysis of the combined methylene chloride extracts was made. The following products resulted with a yield related to the amount of acetaldehyde diethylacetal (A) used or to the amount of hexamethylenetetramine (F) used, depending on the aldehyde need: pyridine, 0.9 percent (A); 3-picoline, 57.7 percent (F); 3-ethylpyridine, 15.6 percent (A); 2,5-lutidine, 2.9 percent (A); 3,5-lutidine, 1.3 percent (F); and 2-methyl-5-ethylpyridine, 1.2 percent (A).

EXAMPLE 13

1140 ml of an aqueous solution containing 397.1 g of dipotassium hydrogen phosphate and 42.6 g of ammonia (pH solution=11.8) was heated in a 2-liter autoclave to 230° C. and stirred at 1500 rpm. A mixture of 117.2 g of acetaldehyde and 213.3 g of a 30.2 percent aqueous formaldehyde solution was pumped into this solution continuously within a period of 63 minutes (molar ratio=1:0.81). At the same time the reaction pressure varied between 35 and 33 bar. After complete addition of the aldehyde mixture, the reaction mixture continued to be stirred for 10 minutes at 230° C. and was then cooled to ambient temperature. Finally, the developed organic phase was separated, the aqueous phase was extracted three times with 100 ml of methylene chloride, the extracts were combined with the above-mentioned organic phase and the aqueous phase, which during this time had been again separated, was extracted with additional 60 ml of methylene chloride. The gas chromatographic analysis of the altogether five combined organic layers resulted in the following products with a yield related either to the amount of acetaldehyde (A) used or to the amount of formaldehyde (F) used, depending on the aldehyde need: pyridine, 1.7 percent (A); 3-picoline, 46.4 percent (F); 3-ethylpyridine, 10.4 percent (A); 2,5-lutidine, 4.2 percent (A); 3,5-lutidine, 2.9 percent (F); and 2-methyl-5-ethylpyridine, 1.0 percent (A).

All of the gas chromatographic analyses were carried out with the use of an internal standard as well as with due consideration of ths surface correction factors.

EXAMPLES 14 to 17

Examples 14 to 17 were conducted basically in the same manner as in Example 13, with the details thereof being set out in the following table:

temperature of 180° to 280° in a closed vessel in the presence of ammonia and/or ammonium ions and in the presence of an anion or anions of inorganic and/or organic acid or acids, which at 20° C. have an acid dissociation constant of $10^6$ to $10^{-12}$.

2. Process as claimed in claim 1 wherein (i) an acetaldehydeacetal and (ii) a formaldehydeacetal is used in a molar ratio of from 1:0.5 to 1:1.2.

3. Process as claimed in claim 2 wherein the anions of the inorganic and/or organic acid or acids are inserted by the addition of the corresponding water-soluble sodium or potassium salts of said inorganic and/or organic acid or acids into the reaction solution.

4. Process as claimed in claim 3 wherein the reaction is conducted at a temperature from 205° to 240° C.

5. Process as claimed in claim 4 wherein the salts are used in an aqueous solution in a concentration of 0.3 to 10 mole/l.

6. Process as claimed in claim 1 wherein the first educt is acetaldehyde acetal.

7. Process as claimed in claim 1 wherein the second educt is formaldehyde acetal.

8. Process as claimed in claim 1 wherein the second educt is hexamethylenetetramine.

9. Process as claimed in claim 1 wherein (i) an acetaldehydeacetal and (ii) a formaldehydeacetal are used in a molar ratio of from 1:0.8 to 1:1.

10. Process as claimed in claim 1 wherein (i) an acetaldehydeacetal and (ii) hexamethylene-tetramine are used in a molar ratio of from 1:0.083 to 1:0.2.

11. Process as claimed in claim 1 wherein the starting pH is between 5.0 and 12.5.

12. Process as claimed in claim 1 wherein the reaction is conducted at a temperature of 205° to 240° C.

13. Process as claimed in claim 1 wherein 0.5 to 3 moles of ammonia and/or ammonium ions are used per mole of the educts.

| Example No. | Salt | Salt, g | NH₃, g | pH | CH₃CHO, g | CH₂O— solution, g | CH₂O— content, % | Mole Ratio | Duration of dosing | Pressure Bars |
|---|---|---|---|---|---|---|---|---|---|---|
| 14 | KH₂PO₄ | 155.1 | 85.1 | 10.6 | 117.6 | 213.3 | 30.5 | 1:0.81 | 65 min. | 40–38 |
| 15 | NaHSO₄.H₂O | 157.4 | 85.1 | 9.2 | 117.3 | 213.3 | 30.5 | 1:0.81 | 65 min. | 38–37 |
| 16 | NaF | 47.9 | 85.1 | 12.2 | 117.2 | 213.3 | 30.5 | 1:0.81 | 67 min. | 36–34 |
| 17 | CH₃COONa | 187.0 | 42.6 | 12.1 | 117.6 | 313.3 | 30.5 | 1:0.81 | 60 min. | 32–30 |

EDUCT QUANTITY AND REACTION CONDITIONS

Yields %

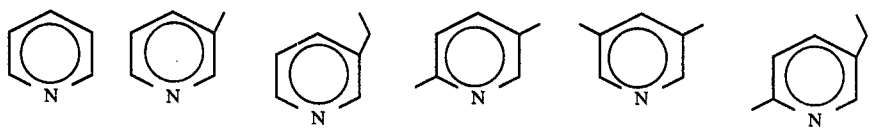

| Example No. | (A) | (F) | (A) | (A) | (F) | (A) |
|---|---|---|---|---|---|---|
| 14 | 1.5 | 60.3 | 16.4 | 4.2 | 1.4 | 1.3 |
| 15 | 1.9 | 56.2 | 13.9 | 5.2 | 1.1 | 1.5 |
| 16 | 2.5 | 43.3 | 9.4 | 4.4 | 2.5 | 1.1 |
| 17 | 2.4 | 41.0 | 7.3 | 4.0 | 2.4 | 1.0 |

What is claimed is:

1. Process for the production of 3-picoline, characterized in that a first educt, consisting of (a) at least one acetaldehydeacetal, (b) at least one acetaldehydeacetal and acetaldehyde or (c) at least one acetaldehydeacetal and crotonaldehyde, is reacted with a second educt, consisting of (d) at least one formaldehydeacetal, (e) at least one formaldehydeacetal and formaldehyde, (f) hexamethylenetetramine or (g) hexamethylenetetramine and formaldehyde, in a liquid, aqueous phase at a 14. Process as claimed in claim 1 wherein 0.1 moles to 3 moles of said at least one water-soluble alkali metal salt of an inorganic and/or organic acid or acids which provides said anion or anions of said inorganic and/or organic acid or acids are used per mole of the educts.

15. Process as claimed in claim 1 wherein 3-picoline is separated from the reaction mixture.

16. Process for the production of 3-picoline, which comprises reacting a first educt, consisting of (a) at least one acetaldehydeacetal, (b) at least one acetaldehydeacetal and acetaldehyde, or (c) at least one acetaldehydeacetal and crotonaldehyde, with a second educt, consisting of (d) at least one formaldehydeacetal, (e) at least one formaldehydeacetal and formaldehyde, (f) hexamethylenetetramine or (g) hexamethylenetetramine and formaldehyde, in a liquid, aqueous phase at a temperature of 180° to 280° C. in a closed vessel in the presence of ammonia and/or ammonium ions and in the presence of at least one water-soluble alkali metal salt of an inorganic and/or organic acid or acids which provides an anion or anions of said inorganic and/or organic acid or acids, which at 20° C. have an acid dissociation constant of $10^6$ to $10^{-12}$.

17. Process as claimed in claim 16 wherein a homogenization agent is present and the composition has a pH of 5 to 12.5.

18. Composition comprised of (i) a member of the group consisting of (a) at least one acetaldehyde acetal, (b) at least one acetaldehyde acetal and acetaldehyde, and (c) at least one acetaldehydeacetal and crotonaldehyde, and (ii) a member of the group consisting of (d) at least formaldehydeacetal, (e) at least one formaldehydeacetal and formaldehyde, (f) hexamethylenetetramine, and (g) hexamethylenetetramine and formaldehyde, (iii) water, (iv) ammonia and/or ammonium ions, and (v) an anion or anions of said inorganic and/or organic acid or acids, which at 20° C. show an acid dissociation constant of $10^6$ to $10^{-12}$.

19. Composition as claimed in claim 18 wherein a homogenization agent is present and the composition has a pH of 5 to 12.5.

* * * * *